(12) United States Patent
De Pablos Almazan

(10) Patent No.: US 12,383,409 B2
(45) Date of Patent: Aug. 12, 2025

(54) VERTEBRAL PROSTHESIS

(71) Applicant: Rodrigo De Pablos Almazan, Madrid (ES)

(72) Inventor: Rodrigo De Pablos Almazan, Madrid (ES)

( * ) Notice: Subject to any disclaimer, the term of this patent is extended or adjusted under 35 U.S.C. 154(b) by 326 days.

(21) Appl. No.: 17/623,524

(22) PCT Filed: Mar. 20, 2020

(86) PCT No.: PCT/ES2020/070196
§ 371 (c)(1),
(2) Date: Dec. 28, 2021

(87) PCT Pub. No.: WO2021/001581
PCT Pub. Date: Jan. 7, 2021

(65) Prior Publication Data
US 2022/0354660 A1    Nov. 10, 2022

(30) Foreign Application Priority Data

Jul. 3, 2019   (ES) ................................ ES201930616

(51) Int. Cl.
*A61F 2/44*    (2006.01)
*A61F 2/30*    (2006.01)

(52) U.S. Cl.
CPC ............ *A61F 2/44* (2013.01); *A61F 2/30942* (2013.01); *A61F 2002/30433* (2013.01); *A61F 2002/30563* (2013.01); *A61F 2002/30581* (2013.01); *A61F 2002/30985* (2013.01)

(58) Field of Classification Search
CPC .................... A61F 2/44; A61F 2/30942; A61F 2002/30433; A61F 2002/30563; A61F 2002/30581; A61F 2002/30985; A61F 2002/443; A61F 2002/30565; A61F 2002/30566; A61F 2002/30568
See application file for complete search history.

(56) References Cited

U.S. PATENT DOCUMENTS

| | | | |
|---|---|---|---|
| 2006/0094951 A1 | 5/2006 | Dean et al. | |
| 2007/0093901 A1* | 4/2007 | Grotz .................... | A61F 2/4611 623/17.11 |
| 2010/0324688 A1 | 12/2010 | Doty | |
| 2012/0045766 A1 | 2/2012 | Nakamura et al. | |
| 2014/0277469 A1 | 9/2014 | Baynham | |
| 2020/0078190 A1* | 3/2020 | Rogers .................. | A61F 2/4455 |

* cited by examiner

*Primary Examiner* — Dinah Baria
(74) *Attorney, Agent, or Firm* — Patenting Consulting Group; Roberto J Rios

(57) ABSTRACT

The invention relates to a vertebral prosthesis with outstanding functionality, adaptability, and safety with respect to its predecessors. It is conceived and designed to provide a better service and serve as an axis so that spinal operations, as well as other diseases can be better addressed. It seeks, above all, to adapt to the nature of human biology and resembles that nature as much as possible, based on an internal suspension system which allows greater mobility and better weight distribution, imitating the natural deformation of the bone.

9 Claims, 3 Drawing Sheets

VERTEBRAL PROSTHESIS

TECHNICAL SECTOR

The present invention relates to a vertebral prosthesis, intended for replacing/substituting a segment of the damaged spine.

The object of the invention is to provide a prosthesis that not only resembles the spinal segment that it replaces, but also behaves as such, that is, it enables better weight distribution, imitating the natural deformation of the bone with respect to the weight to which it is subjected, by virtue of an internal suspension system.

Another object of the invention is to provide a prosthesis the implantation of which is as simple and safe as possible, taking into account the delicacy of the area to be treated.

The invention is therefore situated in the field of biotechnology.

BACKGROUND OF THE INVENTION

Paul Harrington in the 1950s and Eduardo Luque in the 1970s designed their namesake implants to avoid the complications of casting on their patients who were being treated for scoliosis. These implants subsequently spread to fractures, tumours, and degenerative problems.

Until the 1990s, in different hospitals, patients with a vertebral body fracture or tumour who did not improve with the techniques received were subjected to laminectomies and other surgeries that did not solve the symptoms exhibited by the patient.

Currently there are a large number of spinal prostheses, depending on the patient's need, which encompass the complete replacement of the vertebral body, a replacement of the frontal section, or a partial replacement of different structures. In turn, other pathologies are treated by other means, such as cementing or the use of surgical balloons within the same.

The current main vertebrae are structures that form an anchoring at the affected vertebral level, being attached by means of rails to the bodies of the upper and lower vertebrae, providing greater stability but also producing limitations to the degree of movement of the segments that are affected by the intervention as well as the adjacent ones.

As a common feature, these prostheses focus on bone stabilisation, sacrificing movement and functionality against that same balance within the spine.

More specifically, the current technical problems are: rigidity at the levels wherein the prosthesis is applied due to the aforementioned rails, the little or no protection of the medullary canal, and the lack of imitation of the functionality of the anatomical structure that is replaced, and consequently, the decrease of the capacities of the spine in general.

DESCRIPTION OF THE INVENTION

The prosthesis contemplated herein provides a completely satisfactory solution to the problem set out above, enabling greater mobility and better weight distribution, imitating the natural deformation of the bone with respect to the weight to which it is subjected, by virtue of an internal suspension system.

For this, the prosthesis of the invention will be obtained from 3D printing processes of the segment to be replaced from previous radiological studies of the patient.

This makes it possible to accurately reproduce the structures that would normally generate stability in the spine, as well as help to carry out or limit the movement of said segment.

These structures include: vertebral apophyses, as well as other bony projections, which would be copied as they would be in the healthy vertebra, the ligaments, which would be replaced by artificial ligaments that would run through areas determined in the invention to ensure that they properly perform the function, and the vertebral body, which will ensure weight distribution, as well as have a surface that would adapt to the different anchorings in the event of needing the adherence of an intervertebral disc prosthesis.

More specifically, the prosthesis of the invention will be segmented into four portions, divided into two upper and two lower portions, so that these elements are secured in the attachment thereof by means of an assembly of anchorings and screw connections, all of which will provide greater manoeuvrability for the surgeon around the area to operate, enabling the spinal cord to be surrounded and secured without endangering it.

According to one of the fundamental features of the invention, it has been envisaged that the prosthesis includes an internal hydraulic suspension system, which will be applied only to a small lower segment of the vertebra, corresponding to just under 1/3 of the total height thereof, which would enable a more natural weight distribution as well as imitate the natural deformation of the bone with respect to the weight that is impinged therein, changing and gaining space according to the posture, thanks to the very mechanism of the hydraulic suspension.

In this way, a prosthesis is obtained that enables a more optimal imitation of the biomechanical changes of the spine, better managing the forces that impinge on it and providing greater stability, functionality, and spinal protection than its predecessors.

DESCRIPTION OF THE DRAWINGS

As a complement to the description provided below, and for the purpose of helping to make the features of the invention more readily understandable, in accordance with a practical preferred exemplary embodiment thereof, said description is accompanied by a set of plans which, by way of illustration and not limitation, represent the following.

PREFERRED EMBODIMENT OF THE INVENTION

Figure 1:
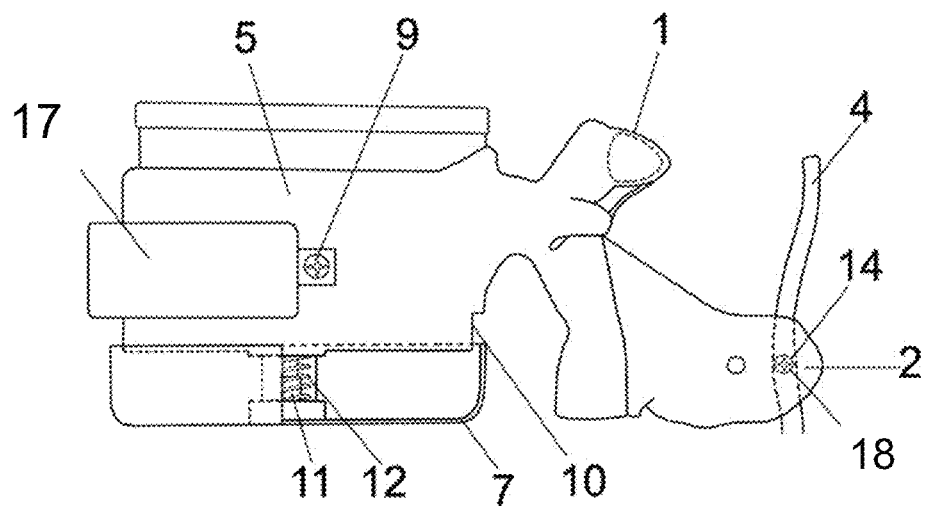
FIG. 1 shows a side elevation view of a vertebral prosthesis made according to the object of the present invention, in the example chosen for the replacement of a segment of the L3 vertebra, since said vertebra is the most commonly affected segment in interventions of this type, a figure wherein the lower part involved in the prosthesis appears partially cross sectioned, in order to be able to view the internal shock absorbing means.
Figure 2:
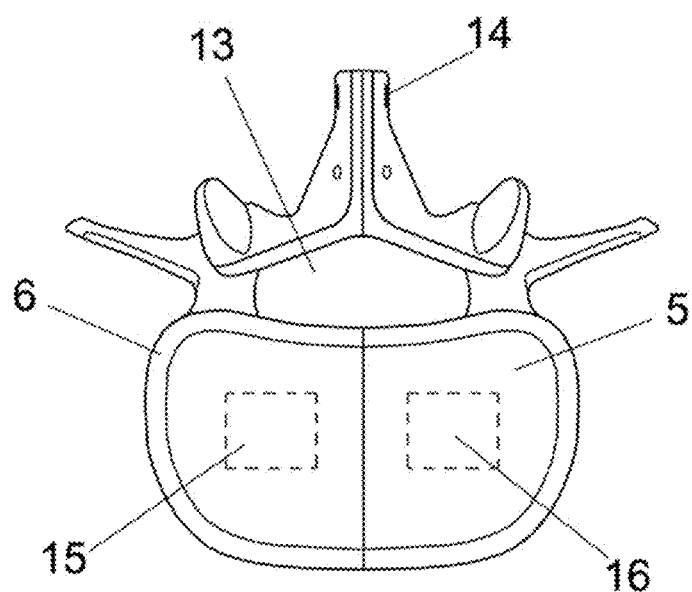
FIG. 2 shows an upper view of the assembly of FIG. 1.
Figure 3:
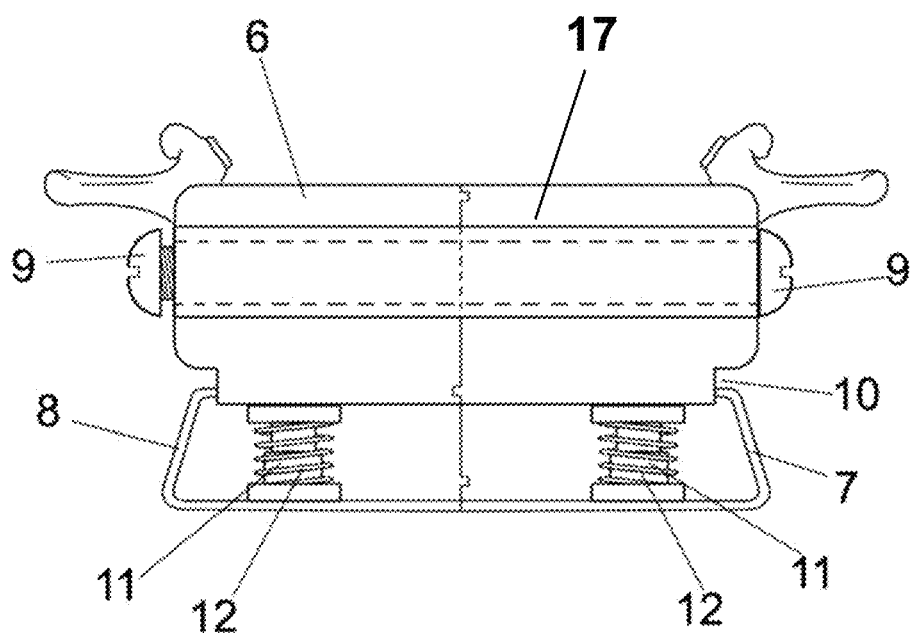
FIG. 3 shows a front elevation and partial cross section view of the prosthesis, to show the internal shock absorbing system thereof.
Figure 4:
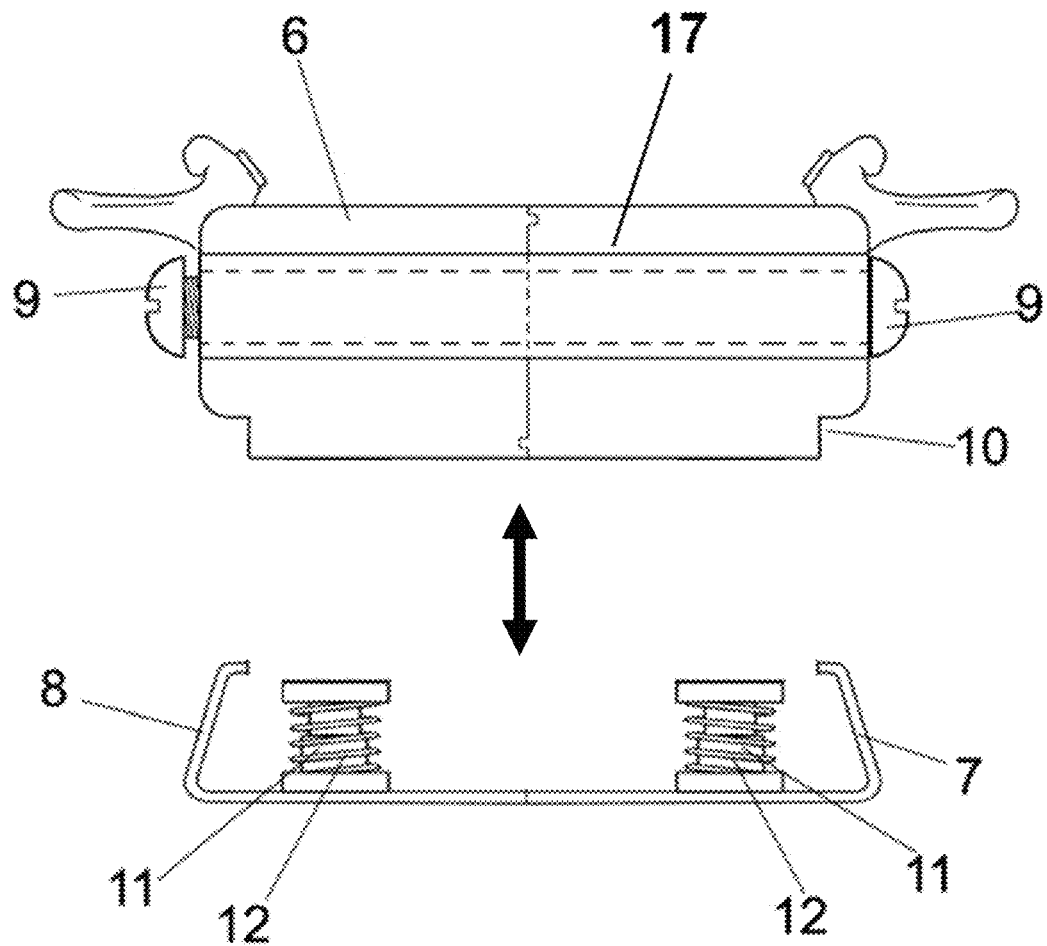
FIG. 4 shows a front elevation and partial cross section view of the prosthesis with the assembly formed by the two lower portions (7-8) being axially displaceable from the upper portions.

Firstly, to obtain the prosthesis of the invention, a radiological examination of the patient, specifically of the vertebra to be treated, would be previously carried out to obtain a 3D image of the vertebra and, from said information and by means of 3D printing processes, obtain the prosthesis.

In this way, structures (1-2) that occur naturally in the vertebra are reproduced in an exact way, functioning as a physical limit to the normal movements of the spine, as well as enabling the use of artificial ligaments (4) on it, to increase this functionality. Said structures that imitate the natural ones enable a better surface anchoring of the musculature, facilitating the aforementioned points even more.

More specifically, the prosthesis of the invention will be segmented into four portions, divided into two symmetrical upper portions (5-6) and two lower portions (7-8) equally symmetrical to each other, which reproduce the physiognomy of the vertebra, and which are tongue-and-grooved coupled to each other, so that the upper portions (5-6) are fixed to each other through a semi-clamp (17) and an attachment/through screw (9), a short lower neck (10) being established in the assembly formed by the two upper portions (5-6), in which the assembly formed by the two lower portions (7-8) is axially displaceable, and the lower portions will exhibit a hollow bowl-like configuration, being linked to the upper portions from a series of suspension elements formed by a hydraulic shock absorber (11) and a spring (12) concentric thereto.

This shock absorbing system enables a more natural weight distribution, imitating the natural deformation of the bone with respect to the weight that impinges therein, changing and gaining space according to the posture.

The distal structure (2) or end of the two upper halves of the prosthesis will exhibit at least one hole (14) for the passage of a fixing screw (18), which also acts as the axis for the interspinous ligament (4).

Finally, it only remains to point out that the upper surface of the upper portions (5-6) could incorporate forms (15-16) for anchoring other types of prostheses, in order to facilitate the anchoring thereof.

The modular nature of the prosthesis means that it can be arranged in a simple, comfortable and safe way around the spinal cord and secure said prosthesis without endangering the spinal cord, a medullary canal (13) of identical configuration to that of a real vertebra being defined between the two upper portions (5-6), but with the aforementioned ease of access to said canal, in addition to facilitating anchoring in a much more fluid and natural way with respect to the spinal cord.

The invention claimed is:

1. A vertebral prosthesis configured to replace a patient vertebra, said vertebral prosthesis comprising:
a body having a shape corresponding to a natural vertebra, said body is formed by two separate symmetrical upper portions that are coupled to each other, and two separate symmetrical lower portions that are coupled to each other forming a hollow bowl-like configuration that is linked to the upper portions from suspension elements located within said hollow bowl-like configuration, wherein a height of said suspension elements is just under $\frac{1}{3}$ of a total height of the vertebral prosthesis.

2. The vertebral prosthesis according to claim 1, wherein said upper portions include a lower neck where the lower portions are axially displaceable in relation to the lower neck of said upper portions.

3. The vertebral prosthesis according to claim 1, wherein said upper portions are coupled to each other by tongue-and-groove coupling means.

4. The vertebral prosthesis according to claim 1, wherein said lower portions are coupled to each other by tongue-and-groove coupling means.

5. The vertebral prosthesis according to claim 1, wherein said two upper portions are secured to each other at an end thereof by a semi-clamp attachment with a screw passing through said two upper portions.

6. The vertebral prosthesis according to claim 1, wherein said upper portions comprise at least one hole located at an end thereof so that a fixing screw is configured to pass through said at least one hole.

7. The vertebral prosthesis according to claim 1, wherein said upper portions further comprise a passthrough hole corresponding to a medullary canal of a vertebra.

8. The vertebral prosthesis according to claim 1, wherein an upper surface of the upper portions comprises sections configured for anchoring other prosthesis.

9. The vertebral prosthesis according to claim 1, wherein said suspension elements comprise a shock absorber and a spring concentric thereto.

* * * * *